United States Patent [19]

Rock

[11] 4,137,011
[45] Jan. 30, 1979

[54] FLOW CONTROL SYSTEM FOR LIQUID CHROMATOGRAPHS

[75] Inventor: John V. Rock, Los Altos, Calif.

[73] Assignee: Spectra-Physics, Inc., Mountain View, Calif.

[21] Appl. No.: 806,591

[22] Filed: Jun. 14, 1977

[51] Int. Cl.² ............................................. F04B 49/08
[52] U.S. Cl. ........................................ 417/22; 417/42; 417/53
[58] Field of Search ........................................ 417/1-5, 417/18, 22, 42-45, 53; 73/23.1

[56] References Cited

U.S. PATENT DOCUMENTS

| | | | |
|---|---|---|---|
| 2,812,773 | 11/1957 | McGee | 417/1 X |
| 3,136,616 | 6/1964 | Thompson | 73/23.1 X |
| 3,446,057 | 5/1969 | Bakalyar et al. | 73/23.1 |
| 3,572,959 | 3/1971 | Shaughnessy | 417/22 X |
| 3,787,882 | 1/1974 | Fillmore et al. | 417/43 X |
| 3,847,507 | 11/1974 | Sakiyama et al. | 417/45 X |
| 3,855,129 | 12/1974 | Abrahams et al. | 417/38 X |
| 3,855,515 | 12/1974 | Hutchins | 417/38 |

Primary Examiner—Robert E. Garrett
Assistant Examiner—Edward Look

[57] ABSTRACT

A flow control system including a pump for delivering a carrier containing isocratic or gradient controlled elution solvents under pressure to a liquid chromatographic column at a substantially constant selected controlled flow rate.

6 Claims, 11 Drawing Figures

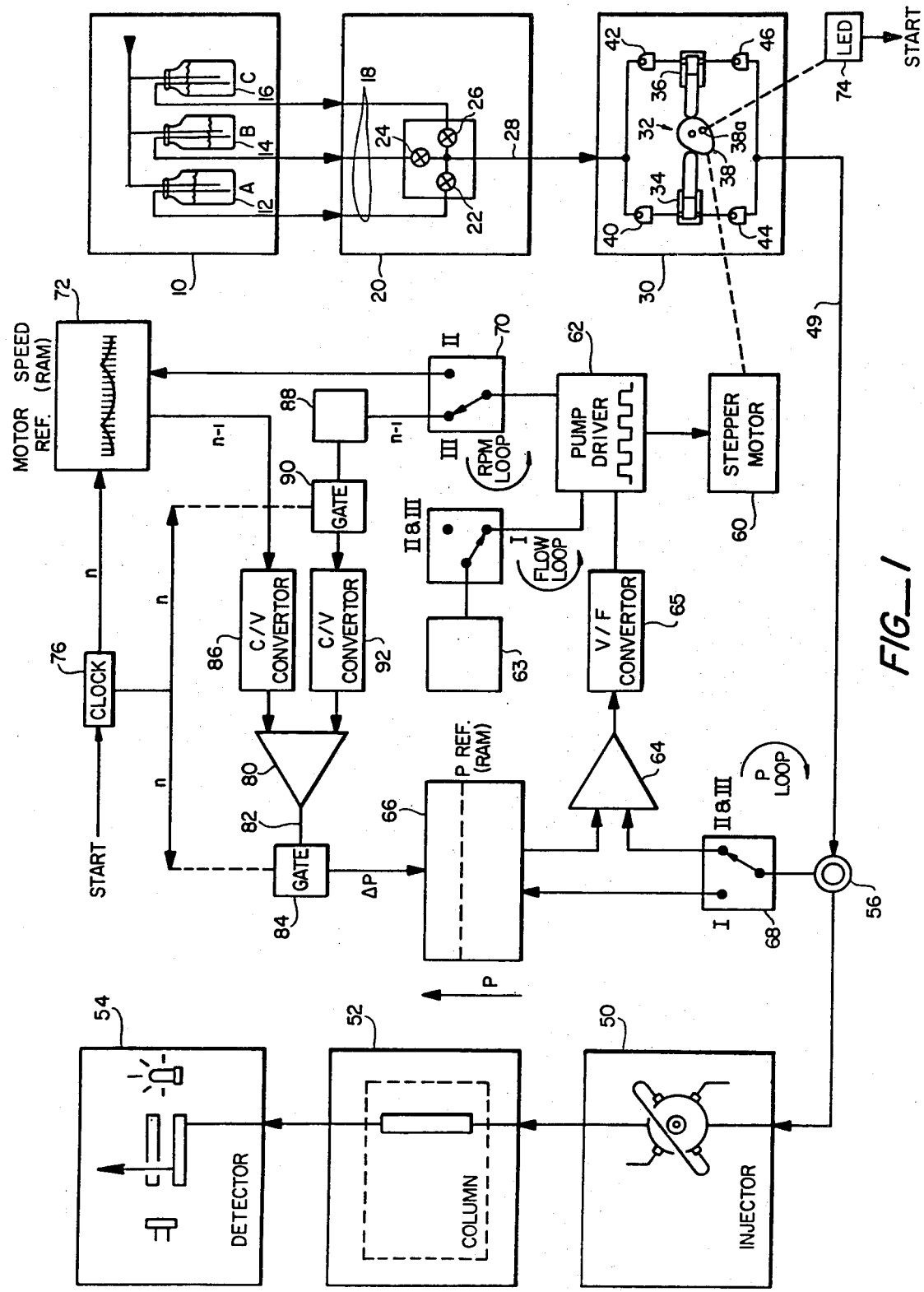
FIG_1

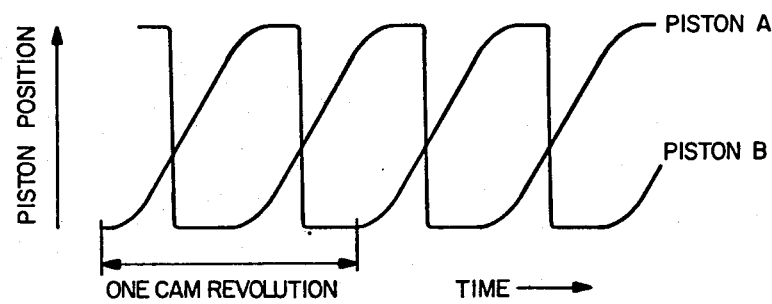
FIG_2
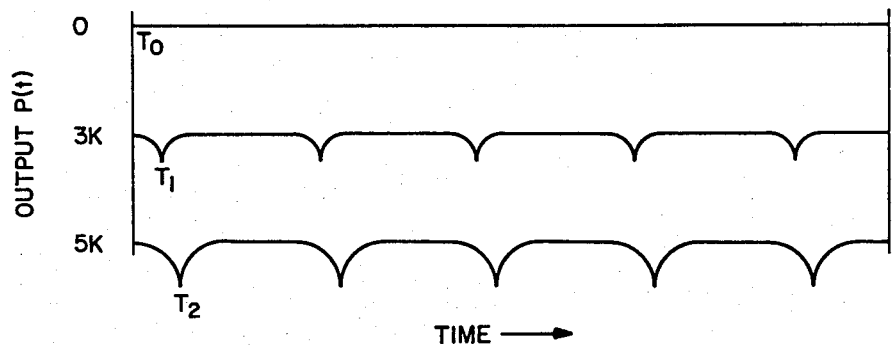
FIG_3A
FIG_3B
FIG_3C
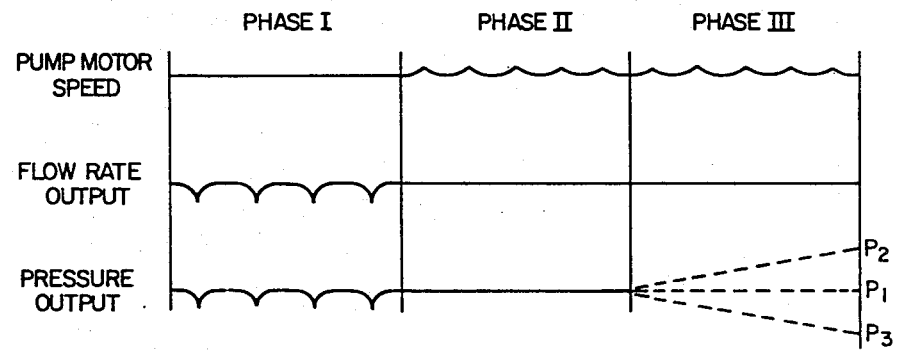
FIG_4A
FIG_4B
FIG_4C
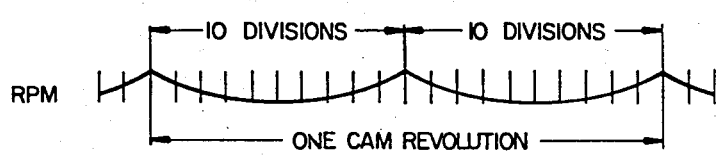
FIG_5

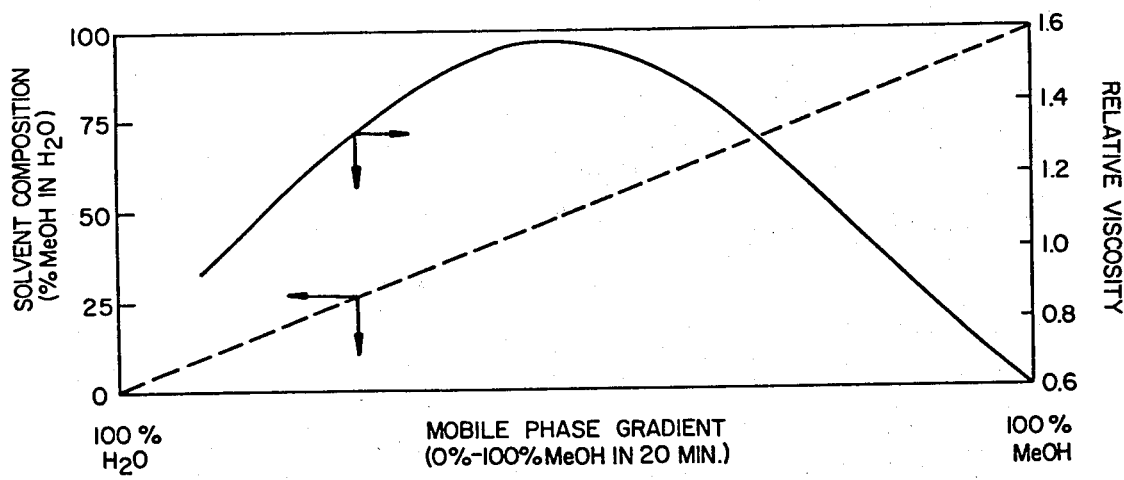
FIG_6
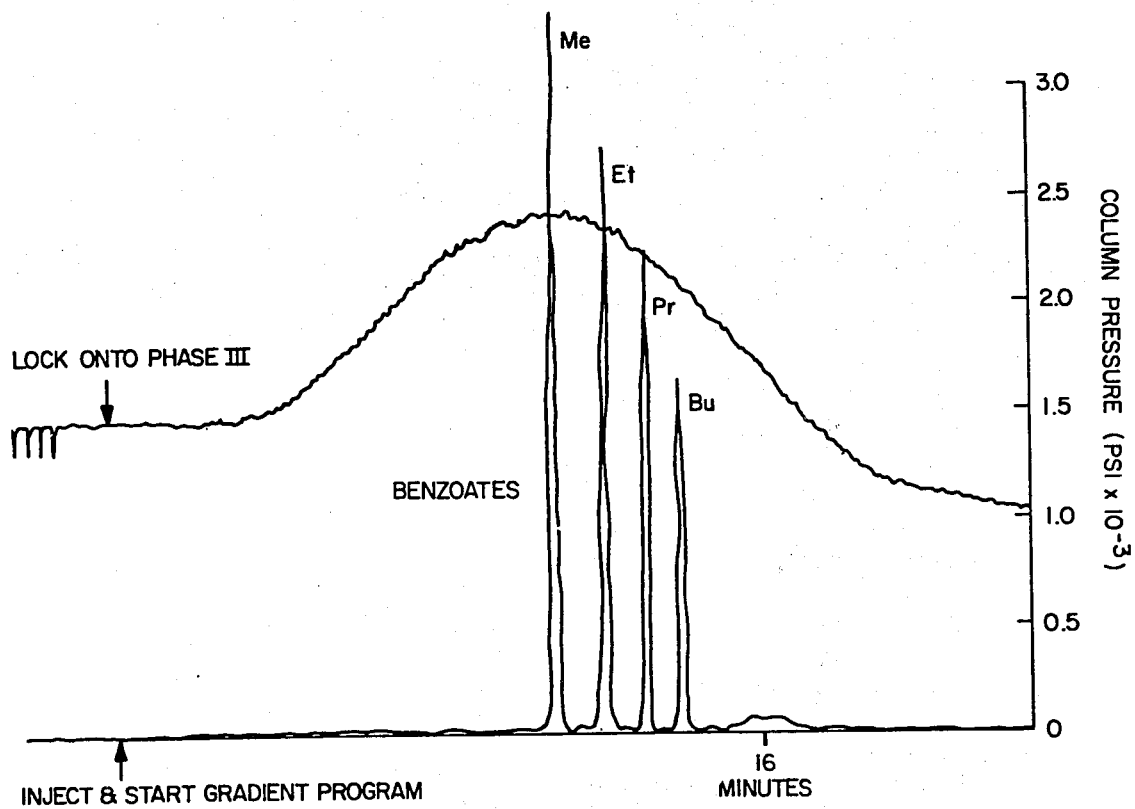
FIG_7

FLOW CONTROL SYSTEM FOR LIQUID CHROMATOGRAPHS

BACKGROUND OF THE INVENTION

This invention relates to flow control systems for use in liquid chromatographs and provides for constant flow of a multi-component carrier liquid under either isocratic or gradient elution modes of operation of the system.

In liquid chromatographic systems used for isocratic and gradient elution, a carrier liquid is used as a mobile phase into which is injected a sample which is transported by the carrier to a stationary phase. Generally, the stationary phase is mounted or packed within a column (LC column) one end of which is provided with a sample injector and connected to the output of a pump for delivering the carrier under pressure thereto. In current high pressure systems the carrier is typically delivered at pressures in the range of about 1,000 to 7,000 psi. The carrier phase in isocratic work contains a fixed proportion of components (for example, 50% water and 50% methanol) while the carrier phase in gradient elution is programmed to vary between the desired values of proportions (for example, from a 90% water/10% methanol to 10% water and 90% methanol) over a predetermined interval of time. In high pressure liquid chromatography (HPLC) the user requires the system to supply a constant flow rate through the column and known proportions or gradient elutions according to settings made in the system and this has been difficult to achieve, particularly in one pump, multiple chamber systems.

It is a primary object of the present invention to provide a liquid chromatographic system which will provide a uniform flow rate through the LC column in both isocratic or gradient operation in accordance with the preset flow rate demand.

In general, the present invention proposes a control system which is particularly adapted to use in multiple chamber single pump systems in which a cam driven by a suitable speed control device such as a stepping motor is connected to a multiple chamber positive displacement piston pump arranged with its chambers and associated pistons in opposition to each other on each side of the cam through an output and fill strokes during each cycle. In a typical such pump the pulsating output strokes of each chamber of the pump are added together and the design of the cam is such that the output strokes overlap and when added through parallel connected output check valves and working into zero pressure, deliver a constant flow for a given drive speed. The inlets to the pump chambers are also connected in parallel through suitable check valves to the output of a composition control module for supplying the carrier liquid in whatever isocratic or gradient proportions selected. The output pressure and flow at the pump when working into a no-load condition is relatively constant. However, in actual systems the pump works against the aforementioned high pressures which causes a non-linear variation in the output of the pump both in the pressure delivered from the pump and in the flow rate which can be produced through a column. This variation is a function of the compressibility and compliance of all of the components involved including the check valve and pump assembly and the compressibility of the solvent carrier components themselves which is a function of several variables including nature of any dissolved gases, and the particular mixture ratios. In themselves, these can be relatively unknown for any arbitrary sets of solvents making up the carrier phase. In addition, the viscosity of the carrier components varies as a function of time in gradient elution work. Also, as the LC column becomes used and can become partially clogged and change its resistance to flow during sample injection and analysis. Many approaches have been taken to controlling the flow through liquid chromatographic systems, examples of which include maintaining a pump motor speed at a constant level as illustrated in the Allington patent U.S. Pat. No. 3,398,689 issued Aug. 27, 1968 and entitled APPARATUS FOR PROVIDING A CONSTANT RATE TO COMPONENT FLOWSTREAM; and by use of a flow feedback loop as illustrated in the Magnussen U.S. Pat. No. 3,917,531 entitled FLOW RATE FEEDBACK CONTROL CHROMATOGRAPH issued Nov. 4, 1975. In general the techniques in the disclosed patents are not adequate to compensate for the pulsation in flow where two or more carrier components are combined and are supplied through a single pump to an LC column. Such pulsations can be caused by mechanical compliance and compressibility or the system, for variations in carrier proportion, and LC column resistance variations; particularly in gradient work wherein the relative viscosity and compressibility of the solvent carrier composition changes as a function of time. There is, therefore, a need for a new and improved flow control system for use in liquid chromatographic systems which will overcome the above limitations and disadvantages.

SUMMARY OF THE INVENTION AND OBJECTS

It is a general object of the present invention to provide a flow control system by which both pulsations and flow changes due to the aforementioned causes are removed so that a generally constant flow is maintained during the operating run of the liquid chromatographic system of the present invention during both isocratic and gradient elution work.

In general, the present invention operates with a one pump multiple chamber system in which the output of the chambers are connected in parallel through input and output check valves respectively. The input check valves are connected to reservoirs of carrier liquid components through a mixing solenoid valve which switches from one position to another to deliver a predetermined proportion of each carrier components to the pump during the intake strokes. The output of the pump is delivered to the input of a sample injector at the head of a LC column, the output of which is passed through a suitable detection system. In the present invention the pressure at the head of the LC column is measured by a transducer serving as the input to a pressure control loop serving as the primary operating control circuit. A first phase (I) of operation maintains constant speed operation of motor and pump and a maximum pressure is measured and selectively stored as a reference from the generally pulsating output at which it is desired to start operation. In a second phase (II) of operation the motor speed is varied to produce an output pressure equal to the reference pressure by a pressure control loop used to drive the pump and produce a reproducable varying speed pattern to constant pressure and flow for a given set of pump and system operating characteristics. This varying speed pattern over a complete pump operating cycle at reference pressure is then stored in a memory. In a next phase (III), a comparison is made at successive intervals of the actual pump speed and that speed stored in memory for each interval of the pump operating cycle. This comparison is used to produce a ratio of the observed variation in pump speed to that stored or expected and this ratio is used during the operating run to adjust a second control loop, labelled herein as a speed reference loop, to update or modify reference pressure loop during the next successive interval. This process is continued iteratively. As a result, if the motor speed within an interval differs from the stored reference value during interval n-1, the value of the reference demand pressure is changed by that ratio in the next interval, n, so that the motor speed on the average is constantly maintained in accordance with the stored pattern and the resultant flow remains substantially constant notwithstanding the compensating changes made to the reference pressure loop and the resultant changes in actual output operating pressure. In this way, viscosity variations or other changes in system variables are eliminated from the resulting flow rate delivered by the pump. For example, should the viscosity decrease substantially, the pressure reference level will be continually reduced by the compared ratio of reference to actual motor speed, so that even though the pressure control loop is active, the average motor speed will be maintained constant, and the actual operating output pressure to the column inlet goes down but the flow remains constant. As a second example, should the resistance of the column increase (such as from gradual clogging resulting from the injeted sample), the pressure reference level will increase so that, even though the pressure control loop is active, the average motor speed is still maintained approximately constant in accordance with the general pattern which is stored in memory, and, in this example, the output pressure of the pump to the column inlet would go up but the flow itself would remain constant.

In general, the system operates to bring the average speed of the pump throughout the run to a constant level which may vary over a short term in order to account for changes in the foregoing system variables. The invention is particularly applicable in gradient elution applications where the viscosity of the carrier composition changes over a wide and complex function.

Among the advantages of the invention include the ability to provide a general high pressure LC chromatograph capable of constant flow operation in isocratic or gradient mode from a plurality of carrier components delivered at low pressure, i.e., substantially at atmosphere pressure, and through a single pumping system as distinguished from multiple parallel connected pumps or pumping systems used for each carrier component. By eliminating the parallel connecting pumping system a significant coat reduction and increase in reliabiity is obtained.

These and other objets and features of the invention will become apparent from the following description and claims when taken in conjunction with the accompanying drawings of which:

BRIEF DESCRIPTION OF THE DRAWINGS

FIG. 1 is a schematic diagram of a flow control system for use in a liquid chromatographic system constructed in accordance with the present invention.

FIG. 2 is a graph depicting the piston stroke pattern for each of the two chambers (A,B) of the pump portion of FIG. 1.

FIG. 3A is a graph showing the output pressure function resulting from combining the output portions of the piston strokes of FIG. 2 and working into a no-load condition.

FIG. 3B illustrates the variation in the output pressure as a function of operating into a significant load as, for example, 3,000 psi.

FIG. 3C is a graph depicting the output pressure as a function of the pump combined output when working into a load of, for example, 5,000 psi.

FIG. 4A shows the pump motor speed as a function over time of the operation of the control system of FIG. 1 during the three phases of its operation.

FIG. 4B and 4C show the output flow rate and output pressure over the same time period as FIG. 4A.

FIG. 5 is an enlarged portion of the motor speed and graph illustrating sampling of the same in accordance with the present invention.

FIG. 6 is a graph showing an example of the change in relative viscosity of a two component solvent carrier composition in gradient elution work.

FIG. 7 is a graph showing analysis of certain benzoates using the present invention in a constant flow rate mode (III) while changing the composition and relative viscosity of the carrier mobile phase in accordance with FIG. 6.

GENERAL

Referring now to FIG. 1, the general schematic diagram of the apparatus for the present invention is disclosed and shows the general liquid chromatography system of the present invention together with the flow control circuits used therein. Thus, a solvent stoage module 10 is provided which contains storage containers 12, 14, 16 for the liquid components which will be used to make up the carrier or mobile phase of the sytem. The storage containers or units provide the liquid to the pump module to be described at atmospheric or low pressure. As used herein low pressure means substantially atmospheric pressure and includes any normal head caused by the elevation of the reservoirs above or below (about 3 feet maximum) the pump. These storage units are connected through suitable piping 18 to a composition control module 20 containing digital valves 22, 24, 26 which are programmed during the intake strokes to select over predetermined time intervals liquids from each of the storage units and for passing the same through a common mixing channel 28 to a flow control pump module 30. The pump module 30 generally includes a single positive displacement pump 32 having opposed pump chambers 34, 36 containing positions A, B driven by and in conformance with the shape of the cam 38 centrally disposed between them. While two pump chambers and a single cam are disclosed, the principle of the invention will be found to be applicable to one or a plurality of pump chambers, particularly when driven from a single power source.

The inlets to pump chambers are provided with inlet check valves 40, 42, the valves in each respective inlet line being connected in parallel to the output 38 of the composition control module. The output of the pump chambers are connected through parallel connection check valves 44, 46 and output line or channel 49 to a sample injection module 50 at the head of an LC column module 52, for separation, the output of which is detected in known manner by a detection module 54 using light transmission techniques or other detection techniques. At the inlet end of the LC column 50 and injector 52 is located a flow-through pressure transducer 56 although a by-pass (or T-connected) pressure transducer can be used if desired. The output signal of the pressure transducer forms one basis for the measurements and control portions of the flow control circuit as herein set forth. As used herein, check valve is defined as a valve which opens in response to liquid pressure and flow thereacross, the threshold of opening and closing occurring upon a development of slight pressure difference across the valve.

Assuming that the cam rotates at a predetermined constant angular rotational speed, the output of the pump as shown in FIG. 2 consists of pulsations caused by the reciprocation of pistons A and B. By suitable cam design, the pulsating output when added together through the check valve means and working into no-load condition approximates a straight line of constant flow (FIG. 3A). During the portion of the pump cycle that the cam is receding represents a return or fill stroke during which the check valves reverse in operation and the respective pump chamber draws the mobile carrier phase from the composition control module in accordance with the programming of the valves therein. While several means of rotating the cam are possible, it is convenient to rotate the same via a stepping motor 60 which is mechanically connected to the cam and driven by pulses derived from a pump stepping motor pulse driver or generator 62 having an output of pulses the frequency of which is variable and controlled by the output of a flow rate level controller having a suitable dial setting mechanism. Thus, the speed of the stepping motor can be changed by changing the rate or frequency at which the pump driver delivers stepping pulses to the motor.

FUNCTION OF PHASES I, II, III AND CONTROL LOOPS

The speed of operation of the pump is controlled in accordance with the present invention by a combination of a pressure sensing control loop labelled "P-loop" in the drawings which in turn is controlled and modified in operation by a comparison circuit labelled "rpm loop" sensitive to deviations from a premeasured motor speed pattern known to produce constant flow and pressure for constant conditions.

As shown generally and previously discussed, FIGS. 3B and 3C indicate that as the flow rate from the high pump changes, there develops a pressure variation measurable at the pressure transducer 56 which pressure variation is relatable to undesired pulsations in flow rate which it is desired to remove. Generally, this flow variation is caused by compliance and compressibility of the system components, namely, the check valves, pump seals and parts as well as the compressibility of both the maximum and residual volume of the carrier mobile phase being passed through the pump module 30 and system, and may vary during an operating run by changes in carrier viscosity, temperature, column impedance or other causes.

The present invention provides a three phase sequence of operation which results in its operating phase (III) in the flow rate being held constant and generally following a predetermined motor speed drive pattern for initially calibrated constant pressure and flow, while allowing the controlling pressure, P-loop to vary demand in response to system variable changes.

More particularly, in an initial phase (I) the motor speed is held constant and an initial reference pressure, shown as P-reference in FIG. 4A is selected and stored in a memory, for a given initial set of conditions and desired flow rate. In the second phase (II) the pressure control loop is activated to produce constant pressure output, which under stable conditions of viscosity, temperature, column impedance, system compliance, carrier compressibility, etc. will also result in constant flow. In this control phase (II) the pump flow and pressure fluctuations (FIG. 3B, 3C) are eliminated (see FIGS. 4A, 4B, phase II).

Also in phase (II), the pattern of motor speed variations required to hold the pressure and flow constant are stored in a memory over a complete operating cycle of the pump. Conveniently, this is done as discrete numbers of motor steps counted over intervals of equal time during the cycle.

In the third phase (III) of operation, during an operating run, the speed of motor operation is compared interval-by-interval to the stored value to ascertain changes in motor speed from the stored pattern caused by changes in system variables. This difference is developed by the "rpm" control loop into a signal and used to override or change the value P-ref set into the first or P-loop memory on an interval-by-interval basis so that the pressure is allowed to vary in response to changes in system variables but the flow rate and motor speed are held constant at nearly the values of the pattern.

P-LOOP AND PHASE (I)

The pump driver 62 responds to the output of a differential amplifier or comparitor circuit 64 which is taken through a voltage to frequency converter 65 to provide a demand signal which results from comparing the measured value of the pressure from pressure transducer 56 with a predetermined pressure reference (P-ref) supplied by a module 66 which includes a read-write (RAM) memory capable of being changed or modified. Comparator 64, voltage to frequency converter 65, pump driver 62, stepping motor 60, and pressure transducer 56 form a first control loop (P-loop) whenever a switch 68 is closed to connect the output of transducer 56 to comparator 64.

In phase (I) operation, switch 68 is connected to another input (memory storage) of module 66 and delivers the pressure sensed by the transducer thereto. In phase (I) a desired flow rate is set into the pump driver by flow rate controller 63 at the level desired. The driver operates to advance the stepping motor and cam through successive cycles of operation of the pump and the pressure and flow is developed through line 49 in the system. The pressure and flow function are shown in FIG. 4A phase (I) and illustrate the pulsations previously described. The pressure developed and sensed by transducer 56 is stored as a pressure reference in module 66 which will be used as the base for successive phases of operation to be described.

PHASE (II) OPERATION

In phase (II) of the operation of the present invention, switch 68 is closed to deliver the output of pressure transducer 56 to one side of comparator 64 and a switch 70 is closed to deliver the pump driver signal to a motor speed reference memory (RAM) 72. The operation of the system is continued, the pressure reference memory 66 supplying a demand pressure which is followed by changes in the pump driver speed caused by any fluctuations appearing in the pressure output. FIGS. 4A and 4B show that in phase (II) operation the pressure is held constant at the demand level while the motor speed or its equivalent the frequency of the pump driver is allowed to vary to develop a motor drive speed pattern which compensates for the otherwise existing pulsations in output pressure and flow. This repeating pattern recurs through each complete operating cycle of the pump and is memorized through a complete operating cycle by memory 72. In the embodiment shown, the present invention utilizes a digital system for driving the motor and a partially digital system for measuring the motor speed fluctuation pattern required to obtain constant flow output and constant pressure. Thus, the rpm speed pattern which is produced is indicated as having values ... Sn-1, Sn ... as a variation in time intervals and as a function of the cam location as it progresses from a reference position. The reference position may be optically indicated by interrupting a suitable LED circuit 74 which senses a hole or other interruption 38A on cam 38 to provide a start pulse which is delivered to a clock 76. Clock 76 supplies interval pulses ... n-1, n ... for indicating each interval of time of operation through the operation of a complete cycle, such pulses being used to synchronize the operation of the apparatus as will be described.

RPM LOOP

Means is provided for making a comparison stepwise during successive intervals in the operation of the system of the present invention between the speed pattern memorized and stored in that interval from phase (II) of the operation of the device with the actual speed at the demand pressure during the successive interval and for changing the demand pressure so as to hold the motor speed in correspondence with the pattern and the flow output constant. Such means is generally indicated as an rpm loop in the drawing and includes a comparator 80, the output 82 of which is connected through a synchronizing gate 84 to an input of the pressure reference module 66 and supplies a ΔP signal thereto which changes the reference pressure stored to give a new, or updated, output demand pressure to comparator 64 during the operating phase (III).

One input of comparator 80 is connected through a count-to-voltage converter 86 to an output of memory 72. The other input of comparator 80 is connected to means for counting the driving pulses actually delivered during an interval n of pump operation. The latter means includes a counter 88 the output of which is delivered through a synchronizing gate 90 and count to voltage converter 92 to that input of comparator 80. Clock 76 provides synchronizing pulses ... n-1, n ... so as to operate gate 90, to access location in memory 72, and to operate gate 84 at the output of comparator 80 over the same time interval n. At the end of every interval n, the results of the preceding interval n-1 are used to reset the demanded operating pressure.

OPERATION DURING PHASE (III)

In phase (III) switch 70 connects a portion of the signal from pump driver 62 output to counter 88 while switch 68 continues to maintain P-loop connected and in operation through comparator 64. Interval n is selected and the stored value is delivered from memory 72 to converter 86. The pump driver operates during the interval causing counter 88 to sum up the total number of pulses received. At the end of the interval n gate 90 opens to deliver the number for that interval to the comparator, the output of which passes through gate 84 as a correction in the pressure reference signal for the next successive interval. The next pulse arrives and resets the gates. In this way, the actual count of pulses of each interval of the driving step function is compared with the stored value for that interval. These are labelled Cn-1 and Sn-1 respectively. At the end of each interval a change in demand pressure is computed and used for the next successive interval. By reiterating this process in each interval, the demand pressure supplied by the pressure reference module 66 is varying so as to eliminate pulsations in the output while permitting an overall gradual change in output pressure to accommodate changes in system operating variables (such as viscosity) which would otherwise affect the ability of the pump to deliver constant flow.

As shown and described herein each of the elements of the block diagram of FIG. 1 consists of electronic circuits the nature and functions of which are sufficiently well known so that specific circuit diagrams of digital or analog electronics for carrying out each function of memory, gate, counter, comparator and the like are believed unnecessary to a person skilled in this art and therefore have been omitted for clarity of presentation. For example, P-ref module 66 could be a motor driven potentiometer, motor speed module 72 could be a digital memory.

In summary, FIG. 4A, phase (I) shows the pump motor speed operating at a constant value. FIG. 4B phase (I) shows pump output flow pulsations due to system compliance. FIG. 4C phase (I) shows the resulting pump output pressure pulsations. During phase (I) the maximum pressure observed 88 is stored as the pressure reference. In phase (II) the constant pressure loop is activated, and the pump motor speed is controlled so as to maintain the output pressure equal to the pressure reference. The motor speed is seen to vary approximately in an inverse pattern to the flow and pressure patterns during phase (I). During phase (II) the motor speed pattern is memorized for later use. In phase (III) the motor speed loop is activated, and the actual motor speed is compared to the memorized motor speed, the difference signal being used to update the pressure reference. When this is done, changes in carrier viscosity do not cause a flow change, even though a constant pressure feedback loop is in operation, because the reference pressure is updated to an approximate value. FIG. 4A, B and C phase (III) illustrate what happens when a carrier viscosity change is encountered, such as when a gradient starts through the pumping system.

In FIG. 4A phase (III) and 4B phase (III) the motor speed and flow rate are seen to hold constant, but in FIG. 4C phase (III) the pressure is seen to change which can be understood by the following example:

Suppose that the phase (II) constant pressure rpm curve is divided into 20 time intervals per pump cycle (two strokes) as shown in FIG. 5. Then, the number of stepping motor pulses in each interval are counted and stored in memory, such as by example,

| Time Intervals | Counts |
| --- | --- |
| 1 | 121 |
| 2 | 118 |
| 3 | 116 |
| . | . |
| 9 | 119 |
| 10 | 120 |
| 11 | 118 |
| . | . |
| 18 | 116 |

-continued

| Time Intervals | Counts |
| --- | --- |
| 19 | 118 |
| 20 | 120 |

This table has 20 entries so that the two pump strokes have their characteristics recorded, because check valves and physical tolerances the pump chamber deliveries may not be the same. However, depending on the precision required, the table could be generated for just one pump stroke.

After the counts in the boxes have been recorded during the constant pressure cycle, the constant flow mode of phase (III) begins. The constant pressure value (the peak of the constant rpm pressure pulse) is maintained through the first time interval.

During the duration of the first interval, the number of motor steps are counted by circuit. After the first increment, the number of pulses accumulated are compared to the reference. If the number of counts is less than the reference, then the flow is less than it should have been and the reference pressure is increased for the duration of the next increment. If the counts are greater than the reference then the reference pressure is lowered. This process is repeated at the end of each interval so that the number of motor steps per unit time is modified for changing conditions while the pressure is allowed to make whatever changes are necessary, always within the general framework of the pulsation free pattern stored in memory and if the proper counts per interval are maintained correctly, the system thinks that it is in constant pressure, thereby eliminating compliance errors, but the reference pressure changes to follow viscosity or other changes.

In isocratic operation, constant pressure control operation can be used to keep flow constant. However, if temperature increases, changing viscosity, or if the column begins to clog, the flow can vary. In order to account for temperature or column clogging, a form of the gradient flow control can be employed. The same gradient flow control is used as above except that the amount of pressure change allowed per interval may be limited to a smaller allowed correction. Thus, if a pump valve should leak due to a contaminant, its effect on flow will be minimized.

Referring to FIGS. 6 and 7 there are shown curves of actual operating conditions for a gradient elution of tartrazine in a carrier composition varying from 100% H20/0% MeOh through 0% H20/100% MeOH. The change in viscosity over this carrier gradient is significant and shown in FIG. 6.

The chromatogram is plotted in FIG. 7 together with a plot of column pressure. As shown, the present invention obtained pulsation free operating pressures which were allowed to vary over a wide range to accommodate the viscosity change but the flow rate remained substantially constant.

While there has been shown and described a preferred form of the invention using a multiple chamber pump and parallel connected check valves, it should be understood that the general principles of the invention are applicable to a wide variety of systems having similar characteristics. Thus, the term check valves as used herein should be taken in a broad sense including both the singular and plural as appropriate. Similarly, the pump itself may be of one or a plurality of chambers driven by any suitable means such as the cam shown, gearing and the like.

As used herein cycle refers to any appropriately representative portion of the pump operating characteristics which uniquely relates the speed of operation of the pump driving motor to the pump flow output. For example, for the two chamber pump shown, an appropriate cycle could be 360° as shown or could be an estimate based upon some other representative portion such as that of 180° of cam rotation.

What is claimed is:

1. In a liquid chromatograph system having a motor driven pump for supplying a carrier containing isocratic or gradient controlled elution solvents and for delivering the carrier to an LC column under pressure, a method of flow control of the pump output comprising the steps of measuring pump output pressure over at least one cycle of pump operation at constant pump motor speed to develop a pressure reference level for a given carrier; subsequently varying the speed drive of the pump motor to maintain the output pressure equal to the pressure reference level; measuring the pattern of pump motor speed during a cycle of operation; storing said pattern in a memory to provide a pump motor speed reference, measuring the actual pump motor speed during operation of the system; comparing the pump motor speed reference and actual pump motor speed to obtain a difference signal in speed caused by changes in system variables; continually changing the pressure reference level applied to the pump in response to the difference signal.

2. A method of flow control for liquid chromatographs as in claim 1 in which the pump motor is driven with a pulse stepping motor the speed of which varies as a function of the frequency of pulses delivered thereto, and further in which the motor speed pattern is measured in discrete time intervals, the average pump motor speed over each interval being stored as a pulse count for that interval, and further in which the comparing step is carried out by comparing the actual counted pulses C of one interval of operation to the number of reference pulses S stored in memory for that interval to derive said difference signal, applying this difference signal to change the pressure reference level in the next successive interval to modify the demand pressure applied therein, continuing the foregoing steps during each successive interval of the operation of the pump.

3. In a liquid chromatograph system having an LC column for receiving a sample to be analyzed in a liquid carrier delivered under pressure to the column, a motor driven pump for supplying said carrier containing isocratic or gradient controlled elution solvents, means for controlling the flow of the pump output comprising means for measuring pump output pressure over at least one cycle of pump operation at constant pump motor speed to develop a pressure reference level for a given carrier; means for varying the speed drive of the pump motor to maintain the output pressure equal to the pressure reference level; means for measuring the pattern of pump motor speed during a cycle of operation and for storing said pattern in a memory to provide a pump motor speed reference, means for measuring the actual pump motor speed during operation of the system; means for comparing the pump motor speed reference and actual pump motor speed to obtain a difference signal in speed caused by changes in system variables; means responsive to said difference signal for continually changing the pressure reference level applied to the pump in response thereto to maintain flow constant.

4. Apparatus as in claim 3 in which the pump motor includes a pulse stepping motor the speed of which varies as a function of the frequency of pulses delivered thereto, and further in which the means for measuring motor speed pattern operates over discreet time intervals, the average pump motor speed over each interval being stored as a pulse count for that interval, and further in which the means for comparing the actual counted pulses C of one interval of operation to the number of reference pulses S stored in memory for that interval to derive said difference signal, and in which the means responsive to said difference signal changes the pressure reference level in the next successive interval to modify the demand pressure applied therein.

5. In a liquid chromatograph system means forming an LC column, reservoir means for supplying carrier components at low pressure, a single pump system for taking said carrier components at said low pressure and for delivering the same to said LC column at a high pressure, operative means at said low pressure for selecting isocratic or gradient elution proportions of said carrier components and for supplying the same to said single pump system, means for controlling the flow of the pump output comprising means for measuring pump output pressure over at least one cycle of pump operation at constant pump motor speed to develop a pressure reference level for a given carrier; means for varying the speed drive of the pump motor to maintain the output pressure equal to the pressure reference level; means for measuring the pattern of pump motor speed during a cycle of operation and for storing said pattern in a memory to provide a pump motor speed reference, means for measuring the actual pump motor speed during operation of the system; means for comparing the pump motor speed reference and actual pump motor speed to obtain a difference signal in speed caused by changes in system variables; means responsive to said difference signal for continually changing the pressure reference level applied to the pump in response thereto to maintain flow constant.

6. A liquid chromatography system as in claim 5 in which said pump system includes a piston operated multiple chamber reciprocating pump.

* * * * *